United States Patent [19]
Ohno et al.

[11] Patent Number: 5,874,307
[45] Date of Patent: Feb. 23, 1999

[54] PROCESS FOR INDUCTION CULTURE OF CYTOTOXIC T LYMPHOCYTES HAVING KILLING ACTIVITY AGAINST TUMOR CELLS

[75] Inventors: Tadao Ohno; Shu Qin Liu; Takeshi Todoroki, all of Ibaraki, Japan

[73] Assignee: The Institute of Physical and Chemical Research, Saitama, Japan

[21] Appl. No.: 492,585

[22] Filed: Jun. 20, 1995

[30] Foreign Application Priority Data

Jun. 28, 1994 [JP] Japan .................................. 6-145908

[51] Int. Cl.⁶ .............................. C12N 5/08; C12N 5/00; A61K 35/14
[52] U.S. Cl. ...................... 435/372.3; 435/373; 435/383; 435/325; 424/93.71; 424/534
[58] Field of Search ..................................... 435/373, 383, 435/325, 372.3; 424/93.71, 534

[56] References Cited

PUBLICATIONS

Kawai et al., Cancer Immunol. immunother (1992) 35:225–239, "Additive Effects of Antitumor Drugs and Lymphokine–Activated Killer Cell Cytotoxic Activity in Tumor Cell Killing Determined By Lactate–Dehydrogenase–Release Assay".

Biotherapy 4 (3) : 427–433, 1990.

Naito et al. 1981 Cell Biology International Reports 5 (7) pp. 675–681, Jul. 1981.

Rosenberg et al. 1986 Science 233 pp. 1318–1321, Sep. 19, 1986.

Mukherji et al 1990 Immunological Reviews 116 pp. 33–62, Aug. 1, 1990.

Hayashi et al. 1992 Cancer Immunology and Immunotherapy 34 pp. 419–423, Jan. 1, 1992.

Usuda et al 1993 J Gastroenterology and hepatology 8 pp. 517–523, Jan. 1, 1993.

Liu et al 1995 Nature Medicine 1 (3) 267–271, Mar. 1, 1995.

*Primary Examiner*—Michael P. Woodward
*Assistant Examiner*—Mary K Zeman
*Attorney, Agent, or Firm*—Greenblum & Bernstein, P.L.C.

[57] ABSTRACT

A process for an induction culture of a cytotoxic T lymphocyte having cell killing activities against a tumor cell which comprises the step of coculturing a tumor tissue containing said tumor cell and a lymphocyte of autologous peripheral blood obtained from a subject from which the tumor tissue is derived. The process is convenient since no separation and pure culture of tumor cells is required. The resulting cytotoxic T lymphocyte cells are useful for clinical treatments of tumors, e.g. adoptive immunotherapies.

17 Claims, No Drawings

PROCESS FOR INDUCTION CULTURE OF CYTOTOXIC T LYMPHOCYTES HAVING KILLING ACTIVITY AGAINST TUMOR CELLS

BACKGROUND OF THE INVENTION

1. Field of the Invention

The present invention relates to a process for an induction culture of T lymphocytes having killing activity against tumor cells. More specifically, the present invention relates to a process for cultivation by which T lymphocytes that have cell killing activities against specific tumor cells derived from a tumor patient can be extracorporeally induced and proliferated.

2. Related Art

Cytotoxic T lymphocytes (hereinafter in the specification, "cytotoxic T lymphocyte" may sometimes be referred to as "CTL") have been known as lymphocytes capable of specifically killing tumor cells. Cytotoxic T lymphocytes may be induced and proliferated from mononuclear cell fractions. The cells have extremely high specificity against tumor cells in such a manner that they, even after induction and proliferation, only attack the tumor cells used as a target for CTL induction culture, and that they can never attack other tumor cells.

For induction cultures where CTLs are induced and proliferated by using mononuclear cell fractions from peripheral blood, purely cultured established tumor cell lines or tumor cells separated from a tissue and cultured under conditions of quasi-pure culture have been so far used as the target (target cells). However, there is a problem that tumor cells obtained by using an extirpated human tumor tissue or organ as a starting material may possibly be contaminated with tissue cells other than tumor cells, and that pure cultures are not always available.

Furthermore, there is another problem that purely cultured tumor cells can hardly be established as tumor cell lines unless they are artificially immortalized by, e.g. a treatment using genetic engineering techniques, and that most of tumor cells lose proliferating abilities in subcultures. Moreover, even where a surgically extirpated tumor tissue material is used that obviously contains living tumor cells, it is sometimes observed that the tumor cells cannot be suitable to in vitro culture conditions and die in a few days after the beginning of primary culture. For these reasons, induction cultures of CTLs can not be easily obtained where the establishments of tumor cell line or the primary cultures of tumor cells are difficult. Accordingly, processes are desired by which CTLs can be reliably induced using tumor tissues.

SUMMARY OF THE INVENTION

Accordingly, an object of the present invention is to provide a process for the induction and expansion culture of CTL using peripheral blood as a starting material, in which a raw tumor tissue containing tumor cells is used without separating the tumor cells as a target.

More specifically, the object of the present invention is to provide the process that can achieve a reliable induction culture of CTL derived from peripheral blood, regardless of a success or failure of primary culture of tumor cells and regardless of a kind of the tumor tissue, i.e. a living tissue, or alternatively, a fixed tissue if a living tissue cannot be obtained and a fixed tissue is only available.

The inventors of the present invention conducted various studies to achieve the foregoing objects, and as a result, they found that CTLs specific to tumor cells can be induced by coculturing a tumor tissue, either living or fixed, with a lymphocyte fraction of a patient's autologous peripheral blood from whom the tumor tissue was derived. They also found that the CTLs obtained by the process described above can alone be subjected to successive expansion cultures without losing their tumor cell killing activities after the removal of the tumor tissue. The present invention was achieved on the basis of these findings.

The present invention thus provides a process for an induction culture of a cytotoxic T lymphocyte having killing activities against a tumor cell which comprises the step of coculturing a tumor tissue containing said tumor cell with lymphocytes of autologous peripheral blood obtained from a subject from which the tumor tissue is derived. According to a preferred embodiments of the present invention, there are provided the aforementioned process wherein the subject is a human tumor patient; the aforementioned process wherein a living tissue is used as the tumor tissue; the aforementioned process wherein a fixed tissue is used as the tumor tissue; the aforementioned process wherein a minced fragment or a thin section of a tumor tissue is used as the tumor tissue; the aforementioned process wherein the coculture is carried out at such a cell concentration that the tumor cells in the tumor tissue and the lymphocytes of the peripheral blood can mutually be contacted; and the aforementioned process wherein the coculture is carried out by using a culture medium in which a normal T lymphocyte can be cultured.

The present invention also provides a cytotoxic T lymphocyte obtained by the culture according to the aforementioned process. There is further provided a process in which the cytotoxic T lymphocyte obtained by the culture according to the aforementioned process is subjected to an expansion culture in the absence of the tumor cells. This process is useful since a large number of the cytotoxic T lymphocytes, which are used for e.g. adoptive immunotherapies, can be produced by the process. The present invention further provides a pharmaceutical composition as an anti-tumor agent which comprises as an active ingredient the cytotoxic T lymphocytes obtained by the process described above.

DETAILED EXPLANATION OF THE INVENTION

Tumor tissues used for the process of the present invention are tissues containing tumor cells and can be obtained from, for example, tumor tissue materials surgically extirpated from mammals, for example, monkeys, bovines, horses, rabbits, rats, and mice. Preferably, the tumor tissues are obtainable from tumor tissue materials surgically extirpated from human tumor patients to be treated by an adoptive immunotherapy. For example, the surgically extirpated tumor tissue, per se, may be used as the tumor tissue, or alternatively, the tumor tissue may be cut off from the surgically extirpated tumor tissue. The tumor tissues are not particularly limited provided that the tissues contain tumor cells. All kinds of tissues may be used, which include, for example, living tissues; fixed tissue specimens obtained by fixing treatments of living tissues; residual tissues obtained by removing embedding materials or resins from specimens embedded in embedding materials such as paraffins; and tissues obtained by unfreezing conserved frozen tissues. Among them, living tissues separated from surgically obtained materials immediately after extirpation, or residual tissues obtained by removing embedding materials from thin sections for tissue staining which are derived from fixed tissue specimens using formalin may preferably be used.

Where tumor tissues are used according to the process of the present invention, the aforementioned tumor tissued may preferably used in the form of minced tissue fragments or thin sections. The methods for preparing the minced tissue fragments or thin sections from the tumor tissues are not particularly limited, however, the tissues are preferably cut so that tumor cells are exposed on the sectional surfaces. It is particularly preferred to mince the tissues using tools having sharp top edges such as, for example, surgical scissors, scalpels, and razors. The sizes of the fragments or thin sections of the tumor tissue are not particularly limited. Preferably, the fragments or thin section shaving a maximum thickness of from about 0.0005 to 10 mm, more preferably from 0.002 to 1 mm, may be used.

Where living tissues are used as the tumor tissues, the fragments obtained in the manner described above may be washed with a medium for cell culture. In these cases, the fragments can be washed by incubating the fragments for several days after the addition of interferon τ to the cell culture medium, and followed by discarding the cell culture medium. The concentration of interferon τ is not particularly limited. For example, about 5 ng/ml is preferable.

As the lymphocytes of peripheral blood used for the process of the present invention, lymphocytes can be used which are obtained from peripheral blood of a subject which the tumor tissue containing the tumor cells is derived from. For example, as the lymphocytes of peripheral blood, mononuclear cell fractions can be used that are obtained from autologous peripheral blood of a human tumor patient from whom the tumor tissue is derived. The methods for obtaining the mononuclear cell fractions using peripheral blood as a starting material are not particularly limited, and any methods can be applied provided that T lymphocytes contained in the resulting fractions remain alive.

The process of the present invention is characterized in that the induction culture of CTLs is achieved by coculturing the lymphocytes of peripheral blood with the aforementioned tumor tissue. The methods for the coculture are not particularly limited. For example, cocultures may be carried out in vitro by suspending the above-described mononuclear cell fractions in a cell culture medium, adding the resulting suspension to the tumor tissue fragments obtained in the manner described above, and then culturing the resulting mixture. The coculture may be conducted at a cell concentration that provides mutual contacts of the tumor cells contained in the tumor tissue and the lymphocytes of peripheral blood. For example, the coculture may be carried out by using about 0.1 to 10 times, preferably 0.5 to 2 times of the lymphocytes of peripheral blood based on the tumor cells and at a total cell concentration of 10,000 to 2,000,000 cells/ml, preferably 500,000 to 1,000,000 cells/ml.

Any kinds of the cell culture mediums can be used provided that T lymphocytes can be alive in the mediums. For example, RHAM α medium (Kawai, K., Sasaki, T., Saijo-Kurita, K., Akaza, H., Koiso, K., and Ohno, T., Cancer Immunol. Immunother., 35, pp. 225–229, 1992; described as "LAK medium"), AIM V medium (GIBCO BRL, Life Technologies, INC.), or RPMI-1640, all of which may be added with one or more of various sorts of cytokines, e.g. interleukin-2.

For example, RHAM α mediums supplemented with interleukin-2, interleukin-1, interleukin-4 and/or interleukin-6 may preferably be used. The concentrations of such cytokines are not particularly limited and may be from 1 U/ml to 2,000 U/ml for each of the cytokines. For example, it is preferably to use interleukin-2 at about 67 U/ml, interleukin-1 at about 167 U/ml, interleukin-4 at about 67 U/ml, and interleukin-6 at about 134 U/ml. These four kinds of cytokines may be simultaneously added, or alternatively, each of them may be used alone or in any combinations.

Conditions for the aforementioned coculture may be those well known to one of ordinary skilled in the art. For example, a cultivation temperature may be at from 33° C. to 41° C., preferably 37° C., and an inert gas may be used as an aerial phase which contains a suitable concentration of gaseous carbon dioxide for maintaining the pH of the medium around 7.4 as well as an appropriate concentration of oxygen. The period of time for the coculture is not particularly limited and may preferably be four days or more. Lymphocyte cells induced by carrying out the coculture can be used as the cytotoxic T lymphocytes of the present invention. The details of the method for the coculture of the monocyte fractions and the tumor tissue fragments will be further explained in the following examples. However, the scope of the method of the present invention is not limited to any details of these processes.

According to another embodiment of the present invention, the cytotoxic T lymphocytes obtained by the induction cultures according to the above-described methods can be subjected to successive cultivations after removing the tumor tissues. As a result of the cultivation, a culture mixture containing cytotoxic T lymphocytes expanded by a monolayer culture can be obtained. The cytotoxic T lymphocytes separated from the culture mixture are particularly suitable for all kinds of clinical treatments of tumors including adoptive immunotherapies and for tumor researches. Separation and recovery of the expanded CTLs may be conducted according to methods well known to those skilled in the art. For example, pharmaceutical compositions comprising the resulting cytotoxic T lymphocytes as active ingredients may be manufactured by processes well known to those skilled in the art, which may be administered, e.g. injected to the patients from whom the tumor tissues are derived.

The present invention will be further explained more specifically by the following examples. However, the scope of the present invention is not limited to the examples.

EXAMPLES

Example 1

Induction Culture of CTL From Fresh Tumor Tissues

A tumor tissue of a recurrent brain tumor was obtained asceptically from a 38-year-old male patient at surgical operation. The tumor was diagnosed as glioblastoma multiforme. No contamination of normal brain tissues was found in the removed tumor tissues as observed with naked eyes. The tumor tissues were wetted with a few drops of Dulbecco's modified MEM (DMEM) containing 10% fetal bovine serum, and minced to less than 1 mm in diameter using ophthalmological scissors. The mincing was performed within 4 hr after the surgical operation. A part of the minced tumor tissues was used for the induction culture of CTL, and the remaining part of the minced tumor tissues was stored according to the conventional freezing method for animal cells by immersing in the freeze medium, MEM containing 10% dimethylsulfoxide.

Primary culture of the tumor cells was started by adding 1 ml of culture medium used for common tumor-cell culture with 5~10 minced tumor tissue fragments per well in a plastic 24-well plate. Cells were maintained at 37° C. in humidified 5% $CO_2$-95% sir. The medium was half changed at 2~3 day interval. After 2 weeks, two types of cells attached and grown from the tumor tissues were observed, namely sheet-forming cells and asterocytic cells.

With informed consent, 20 ml of heparinized peripheral blood was harvested from the tumor-bearing patent. Peripheral blood mononuclear cells (PBMC) were separated by the conventional Ficoll-Hypaque method (Lymphosepal, Immune Biomedical Institute Inc., Tokyo), PBMC were washed once with Dulbecco's phosphate buffered saline (PBS) and once with CTL-culture medium consisting of RHAM α medium, autologous blood plasma (5% v/v), interleukin (IL)-1(167 U/ml), IL-2(67 U/ml), IL-4(67 U/ml), and IL-6(134 U/ml). Furthermore, CTL-IFN-τ-culture medium was prepared by adding interferon-τ-(5 ng/ml) to the CTL-culture medium.

CTL induction culture was started by cocluturing the tumor tissues and the autologous PBMC. Fresh tumor tissues minced well to form semi-solid alary were placed in wells of a 6-well plate at approximately 200 μl/well, then the PBMC(5,000,000), suspended in 5 ml CTL- or CTL-IFN-τ-culture medium were added. This coculture were maintained at 37° C. in humidified 5% $CO_2$-95% air. After cocultured for 5 days, remaining large tumor tissues were removed, then lymphoid cells were collected by centrifugation at 1,000 rpm (140×g) for 5 min. The lymphoid cells were then resuspended in fresh CTL-culture medium for both cases of CTL- and CTL-IFM-τ-induction culture. Cultures were contained by changing the CTL-culture medium at 3~5 day interval. Proliferated cells were defined as CTL or CTL-IFN-τ corresponding to the induction medium.

For comparison, PBMC were suspended in LAK-medium at a concentration of 5,000,000 cells in 5 ml, then they were added into a 6-well plastic culture plate at 5 ml per well. The grown lymphocytes were defined as LAK cells. LAK-medium consists of RHAM α medium, autologous plasma (5% v/v), and IL-2(200 U/ml). Other conditions for culture were the same as those for the CTL- and CTL-IFN-τ-induction culture. Results of the induction cultures of CTL, CTL-IFN-τ and LAK were shown in Table 1.

TABLE 1

| Proliferated | Culture period (days) | | | | |
| --- | --- | --- | --- | --- | --- |
| lymphocytes | 1 | 6 | 10 | 13 | 15 |
| LAK | 5000* | 3136 | 6700 | 8350 | 24400 |
| CTL | 5000 | 3600 | 6600 | 10750 | 32800 |
| CTL-IFN-γ | 5000 | 3350 | 5300 | 11050 | 37560 |

*Unit in this Table is 1000 cells/well.

Frozen tumor tissues were thawed and dispersed by treatment with enzymes to prepare tumor cell suspension which was served to measure cytotoxic activity of CTL, CTL-IFN-τ and LAK cultured for 14 days from the start of CTL induction culture. The treatment with enzymes of the thawed tumor tissues was carried out as follows. Approximately 200 mg of tumor tissues was washed with PBS, stirred for 10 min in 40 ml of RPMI-1640 medium supplemented with 10% (v/v) fetal bovine serum, 20 mg collagenase (Sigma, Type I), 0.5 mg deoxyribonuclease (Sigma, Type I) and 2 mg hyaluronidase (Sigma, Type V). Dispersed tumor cells were pelleted by centrifugation at 1,000 rpm for 3 min. After washing once with PBS, tumor cells were resuspended in RHAM α medium containing 5%(v/v) autologous plasma.

The tumor cells and the above mentioned lymphocytes were mixed at a ratio of 1:1.4 and adjusted to 115,000 cells/ml and placed in wells of a 24-well culture plate at 1 ml per well. The mixture was incubated for 48 hr, then number of cells in each well was counted with a hemocytometer. On the other hand, the tumor cells or the lymphocytes were also incubated by themselves for 48 hr in RHAM α medium containing 5% autologous plasma, and the number of cells in each well was also counted. With these cell counts, remaining tumor cells were calculated by subtracting number of lymphocytes from the number of total cells in the mixture. Percentage of the remaining tumor cells to the tumor cells incubated without the lymphocytes was calculated. Measurement of this cytotoxic activity was done on triplicated samples for an observation point, then average and standard deviation (SD) were calculated.

TABLE 2

| Type of lymphocytes | Percentage of surviving tumor cells ± SD |
| --- | --- |
| LAK | 66.6 ± 7.9% |
| CTL | 17.8 ± 16.1% |
| CTL-IFN-γ | −4.6 ± 5.9% |

The CTL were stained with FITC-labelled anti-CD3 monoclonal antibody (Nichirei Co., Tokyo) and observed under microscopy. It was found that 95% of the cells were positively stained. When stained with FITC-labelled anti-CD4 or anti-CD8 monoclonal antibodies (Bekton-Dickinson, Co., USA), 5% or 80%, respectively, of the cells were stained positively.

Example 2

Induction Culture of CTL From Fixed Tumor Tissues

Approximately 250 ml of cancerous ascites was collected from a male 53-year-old patient with a gastric tumor. Un-stained thin tumor sections with 2 μm thickness were obtained from the formalin-fixed paraffin-embedded tissue blocks that have been prepared for pathological inspection when original tumor sites were removed surgically. Pathological diagnosisced was advanced adenocarcinoma derived from gastric mucosa. Furthermore, 20 ml of heparinized peripheral blood was obtained from the tumor-bearing patient with informed consent. LAK cells were prepared from PBMC of the patient as described in Example 1.

Ascitic cells were collected from the tumor ascites by centrifugation at 1,000 rpm for 5 min. Mononuclear cell fraction (containing lymphocytes), tumor cell fraction, and erythrocyte fraction were separated by the conventional Ficoll-Hypaque method (Lymphosepal, Immune Biomedical Institute Inc. Tokyo). The mononuclear cells were cultured at 1,000,000 cells/ml in a TIL-culture medium which was prepared with the CTL-culture medium as described in Example 1 but the 5%(v/v) autologous plasma was replaced to 10%(v/v) fetal bovine serum. After the culture for a week, IL-2 was kept at the concentration of 67 U/ml, but concentrations of IL-1, IL-4 and IL-6 were reduced to 16.7, 6.7, and 13.4 U/ml, respectively. With this modified TIL-culture medium, the mononuclear cells were cultured continuously by diluting properly when necessary. Proliferated cells in this culture were defined as TIL.

The tumor cell fraction was resuspended in DMEM containing 10% fetal bovine serum and adjusted to 1,000,000 cells/ml, then 5 ml of the cell suspension was placed in a 6-cm plastic culture dish. The cells were incubated for 2 days at 37° C. in humidified 5% $CO_2$-95% air. Floating cells were removed and adhered cells were continued to culture with fresh medium. After cultured for a month with periodical medium change, tumor cells became confluent and continued stable growth even after the subculture was continued for over 3 months. Thereafter, this cell line was named GT3TKB.

Autologous PBMC were obtained from the peripheral blood of the tumor-bearing patient as described in Example 1. Approximately 5,000,000 cells of the PBMC were suspended in 5 ml of the CTL-culture medium as described in Example 1. They were added onto the 6,000,000 tumor cells that were previously maintained in a 6-cm plastic culture dish to start the CTL induction culture. The induction was carried out at 37° C. in humidified 5% $CO_2$-95% air. After cultured for 5 days, floating lymphocytes were harvested by centrifugation at 1,000 rpm for 3 min, then resuspended in fresh CTL-culture medium and continued to culture by changing the medium at 3~5 day interval. Proliferated cells were defined as CTL(live), corresponding to live target tumor cells that were used for this CTL induction culture.

The paraffin-embedded cancerous tissue thin sections mounted on slide glasses were washed with toluene and a series of increasing concentrations of ethanol. They were scraped off into a culture dish, sterilized with 70% ethanol, washed three times with PBS, and placed in a well of a 24-well culture plate. Autologous PBMC, obtained as described above, were suspended in the CTL-culture medium (see Example 1) at 1,000,000 cells/ml. One ml of this suspension was added onto the washed sections to start CTL induction culture. Incubation was carried out at 37° C. in humidified 5% $CO_2$-95% air. Half the culture medium was changed every 2 days until the lymphocytes began to grow.

Most of lymphocytes died after cultured for a week, yet lymphocytes attached to the sections had been growing. Lymphocytes that grew and floated in the medium, were collected by centrifugation at 1,000 rpm for 3 min, resuspended in the fresh CTL-culture medium, and continued to culture with periodical change of the medium and transfer to new wells coated with anti-CD3 antibody as described by Shiraiwa (Shiraiwa et al., Biotherapy, 4,427,1990). Proliferated cells were defined as CTL(fix) corresponding to the fixed target tumor cells used for the CTL induction culture.

Surface antigens, such as CD3, CD4, CD8 and CD16, were investigated with FITC-labelled monoclonal antibodies on LAK, TIL, CTL(live) and CTL(fix) obtained as described above. Furthermore, cytotoxicity of these lymphocytes was investigated on live CT3TKB cells used as the target. Results are shown in Table 3.

Suspension of the tumor cells at a concentration of 100,000 cells/ml in DMEM containing 5% fetal bovine serum were prepared. A portion of the cell suspension, 0.1 ml, was seeded in each well of a plastic 96-well culture plate. Culture condition was the same as described above. After cultured over night, the attached live tumor cells were counted and used as the initial cell numbers per well. The medium was replaced to 0.1 ml of an assay-medium containing lymphocytes, then the plate was incubated for further 48 hr. Number of lymphocytes added was adjusted to a ratio (called B/T ratio, hereafter) of 0.5, 1.0 or 2.0 against the number of tumor cells in a well. The assay-medium consists of RHAM α medium supplemented with fetal bovine serum (5%, v/v), IL-1(167 U/ml) and IL-2(67 U/ml).

After incubation for 24 hr, the medium was discarded, and 0.05 ml of 10% (v/v) formalin solution was added to each well to fix the remaining tumor cells and lymphocytes that adhered strongly onto the tumor cells. The plate was washed by immersing in tap water, then, 0.1 ml of 0.4% crystal violet solution dissolved in water was added to each well and stand for 1 hr at room temperature to stain the tumor cells. After the plate was washed with water and dried in air, 0.1 ml of ethanol was added to each well to extract the dye. The amount of crystal violet was determined quantitatively by measuring optical density of each well at 540 nm. For determination of tumor cell-killing activity of the lymphocytes, percentage of remaining attached cells was calculated by using the optical density of the tumor cells to which the lymphocytes were added as numerator and those to which no lymphocytes was added as denominator. Eight replicated wells were used for a point of observation.

The optical density derived from the strongly-adhered lymphocytes on the remaining tumor cells was relatively very small and therefore negligible in the above calculation, that was confirmed by carring out a preliminary experiment in which variable number of the lymphocytes were added to a constant number of the tumor cells, incubated for a while, and then processed the plate to determine the amount of crystal violet as described above. Results of the present experiment revealed that, both CTL(live) and CTL(fix) had the surface antigen CD8 and showed the ability to kill most of the autologous tumor cells GT3TKB.

TABLE 3

| Lympho-cytes | Cell Surface antigens | | | | Tumor-killing activity (E/T = 1) Percentages of remaining tumor cells ± SD |
|---|---|---|---|---|---|
| | CD3 | CD4 | CD8 | CD16 | |
| LAK | 94.6% | 28.1% | 34.0% | 5.4% | 94.3 ± 2.6% |
| TIL | 99.1% | 7.5% | 84.0% | 3.3% | 98.0 ± 3.7% |
| CTL (live) | 97.0% | 3.1% | 93.6% | 0.1% | 1.3 ± 2.3% |
| CTL (fix) | 97.2% | 2.8% | 92.5% | 0.1% | 24.1 ± 1.0% |

*Target cells were GT3TKB cells.

Furthermore, tumor cell-killing activity of CTL(fix) was also examined against other human gastric tumor cell lines provided by RIKEN Cell Tank (Tsukuba Science City, Ibaraki 305, Japan). The results are shown in Table 4. These results show that CTL(fix) possessed ability to kill specifically the autologous tumor cells GT3TKB, yet almost could not kill the allogeneic tumor cells GCIY and could partially kill the HGC-27 cells.

TABLE 4

| Target gastric tumor cells | E/T ratio | | |
|---|---|---|---|
| | 0.5 | 1.0 | 2.0 |
| GT3TKB | 31.9 ± 5.7%* | 9.7 ± 1.9% | 1.7 ± 1.9% |
| HGC-27 | 81.7 ± 5.7% | 35.6 ± 5.4% | 9.5 ± 2.1% |
| GCIY | 135.5 ± 15.4% | 124.8 ± 13.5% | 79.7 ± 6.5% |

*Percentage of remaining tumor cells ± SD

According to the present invention, the cytotoxic T lymphocytes that have tumor cell killing activity against specific tumor cells can be obtained by the extracorporeal induction culture by using the living tissue or the fixed tissue, per se, containing the tumor cells. The process of the present invention is convenient, since no separation of tumor cells from a tumor tissue and no pure culture of the tumor cells is required, and since a rapid and large amount of culture of the desired cytotoxic T lymphocytes can be achieved. The resulting cytotoxic T lymphocytes are useful for adoptive immunotherapies for tumor patients, researches on mechanisms of killing of tumor cells by lymphocytes, genetic therapies by the introduction of exogenous genes into lymphocytes and the like.

What is claimed is:

1. A process for inducing a culture of cytotoxic T lymphocytes having cell killing activities against a tumor cell, comprising in vitro coculturing tumor tissue containing said tumor cell with lymphocyte of autologous peripheral blood obtained from a subject from which the tumor tissue is derived, said tumor tissue being obtained from fixed and sectioned tumor tissue.

2. The process according to claim 1, wherein the coculture is carried out at a cell concentration effective to provide mutual contact of the tumor cells in the tumor tissue and the lymphocytes of the peripheral blood.

3. A process for expanding a culture of cytotoxic T lymphocytes having cell killing activities against a tumor cell, comprising in vitro coculturing tumor tissue containing said tumor cell and lymphocyte of autologous peripheral blood obtained from a subject from which the tumor tissue is derived, said tumor tissue being obtained from fixed and sectioned tumor tissue separating the tumor tissue from the cytotoxic T lymphocyte, and culturing the cytotoxic T lymphocyte in the absence of said tumor cells.

4. The process of claim 1, wherein the tumor tissue is obtained from formalin fixed and sectioned tumor tissue.

5. The process of claim 1, wherein the fixed and sectioned tumor tissue is obtained from frozen tumor tissue.

6. The process of claim 1, wherein the tumor tissue is obtained from fixed and embedded and sectioned tumor tissue.

7. The process of claim 6, wherein the tumor tissue is embedded in paraffin.

8. The process of claim 7, wherein the paraffin is removed from the tumor tissue.

9. The process of claim 3, wherein the tumor tissue is obtained from formalin fixed and sectioned tumor tissue.

10. The process of claim 3, wherein the fixed and sectioned tumor tissue is obtained from frozen tumor tissue.

11. The process of claim 3, wherein the tumor tissue is obtained from fixed and embedded and sectioned tumor tissue.

12. The process of claim 11, wherein the tumor tissue is embedded in paraffin.

13. The process of claim 12, wherein the paraffin is removed from the tumor tissue.

14. A process for inducing a culture of cytotoxic T lymphocytes having cell killing activities against a tumor cell, comprising coculturing tumor tissue containing said tumor cell with a lymphocyte of autologous peripheral blood obtained from a subject from which the tumor tissue is derived, said tumor tissue being obtained from frozen and sectioned tumor tissue.

15. A process for expanding a culture of cytotoxic T lymphocytes having cell killing activities against a tumor cell, comprising in vitro coculturing tumor tissue containing said tumor cell and lymphocyte of autologous peripheral blood obtained from a subject from which the tumor tissue is derived, said tumor tissue being obtained from frozen and sectioned tumor tissue separating the tumor tissue from the cytotoxic T lymphocyte, and culturing the cytotoxic T lymphocyte in the absence of said tumor cells.

16. A process for inducing a culture of cytotoxic T lymphocytes having cell killing activities against a tumor cell, comprising coculturing tumor tissue containing said tumor cell with a lymphocyte of autologous peripheral blood obtained from a subject from which the tumor tissue is derived, said tumor tissue being obtained from fixed and minced tumor tissue.

17. A process for expanding a culture of cytotoxic T lymphocytes having cell killing activities against a tumor cell, comprising in vitro coculturing tumor tissue containing said tumor cell and lymphocyte of autologous peripheral blood obtained from a subject from which the tumor tissue is derived, said tumor tissue being obtained from fixed and minced tumor tissue separating the tumor tissue from the cytotoxic T lymphocyte, removing and culturing the cytotoxic T lymphocyte in the absence of said tumor cells.

* * * * *

UNITED STATES PATENT AND TRADEMARK OFFICE
CERTIFICATE OF CORRECTION

PATENT NO.    : 5,874,307
DATED         : February 23, 1999
INVENTOR(S)   : T. Ohno et al.

It is certified that error appears in the above-identified patent and that said Letters Patent is hereby corrected as shown below:

Column 9,
Line 22 of the printed patent, after "tissue" insert ---, ---.

Column 10,
Line 20 of the printed patent, after "tissue" insert ---, ---.
Line 36 of the printed patent, after "tissue" insert ---, ---.
Line 37 of the printed patent, delete "removing".

Signed and Sealed this

Thirty-first Day of July, 2001

*Attest:*

NICHOLAS P. GODICI
*Attesting Officer*     Acting Director of the United States Patent and Trademark Office